United States Patent [19]

Gross et al.

[11] 4,134,412
[45] Jan. 16, 1979

[54] HAIR SETTING LOTION CONTAINING A CHITOSAN DERIVATIVE

[75] Inventors: Paul Gross; Eugen Konrad, both of Darmstadt, Fed. Rep. of Germany; Herbert Mager, Fribourg, Switzerland

[73] Assignee: Wella Aktiengesellschaft, Darmstadt, Fed. Rep. of Germany

[21] Appl. No.: 743,290

[22] Filed: Nov. 18, 1976

[30] Foreign Application Priority Data

Jun. 18, 1976 [DE] Fed. Rep. of Germany ....... 2627419

[51] Int. Cl.² .......................... A45D 7/00; A61K 7/11
[52] U.S. Cl. .......................................... 132/7; 424/71; 536/20

[58] Field of Search ...................... 424/71, 72; 536/20; 132/7

[56] References Cited

U.S. PATENT DOCUMENTS

| 3,840,656 | 10/1974 | Kalopissis et al. | 424/72 |
| 3,879,376 | 4/1975 | Vanlerberghe et al. | 536/20 |
| 3,904,748 | 9/1975 | Eckert et al. | 424/71 |

OTHER PUBLICATIONS

Chemical Abstracts, vol. 59 (1963), p. 3465c.

Primary Examiner—V. D. Turner
Attorney, Agent, or Firm—Michael J. Striker

[57] ABSTRACT

Hair setting lotion consisting of an aqueous or aqueous-alcoholic solution of a film-forming resin which contains a water soluble salt of chitosan.

6 Claims, No Drawings

HAIR SETTING LOTION CONTAINING A CHITOSAN DERIVATIVE

BACKGROUND OF THE INVENTION

This invention relates to a hair setting agent which contains water soluble salts of chitosan. The preparation has particularly the objective to improve the permanence and shape of the hair style.

Preparations for setting the hair style usually consist of solutions of film-forming natural or synthetic polymers. As natural polymers there can for instance be used shellac, alginates, gelatin, pectins and cellulose derivatives. Among the synthetic polymers there are used for instance polyvinylpyrrolidone, polyvinylacetate, polyacrylic compounds such as polyacrylic acid or methacrylic acid polymerisates, basic polymerisates of esters formed by these two acids with aminoalcohols or the salts or quaternary products of these basic polymerisates, polyacrylonitrile and copolymerisates of such compounds, for instance polyvinylpyrrolidone-vinylacetate.

SUMMARY OF THE INVENTION

The invention resides in a preparation for setting the hair which consists of water-soluble salts of chitosan instead of the usual polymerisates.

The invention also embraces a process of applying this product in an aqueous or aqueous-alcoholic solution followed by an alkalizing treatment.

DISCUSSION OF THE INVENTION AND PREFERRED EMBODIMENTS

It was surprising to find that preparations for setting the hair with excellent properties would be obtained if water-soluble salts of chitosan were used instead of the usual polymerisates. The chitosan salts have the character of cationic resins but have the advantage as against the conventional cationic, anionic and nonanionic resins used for hair setting that they form hard and non-sticky films which similar to keratine are adapted to exchange water vapor with the surrounding atmosphere without changing their properties. This means that hair which was treated with the agency of the invention does not have a tendency to get sticky or to suffer from a reduced strength of the film even in case of high air humidity or increased perspiring of the scalp.

Additionally the dusting-off of resin particles which is frequent when brushing the hair does not occur since the films made with the compound of the invention have an excellent elasticity and since besides the concentration of the chitosan salts necessary for the hair setting operation is comparatively lower than that of the conventional resins. With the usual hair setting preparations the share of resins normally is about 3% by weight in an aqueous or aqueous-alcoholic solution. By comparison the same setting effect can be obtained with the compounds of the invention in an only 1% by weight aqueous or aqueous-alcoholic solution.

It has also been found that the hair treated with the compounds of the invention suffers less from static charges during brushing and combing than hair treated with the conventional setting agents. This difference is particularly pronounced where the conventional hair setting agents are on the basis of anionic or nonionic resins and are therefore apt to be used more frequently in order to obtain the necessary coating strength. The invention has also resulted in considerably improved effects in regard to the permanence of the set style.

The conventional synthetic resins used in hair setting lotions frequently have residues from their synthesis in the form of monomers. These monomeric substances can cause, apart from an unpleasant smell, other undesired effects by reacting for instance with the other components such as the frequently used dyestuffs, in which case discolorations of the preparations occur.

Also, sensitization of the skin as it is well known with the conventional products can occur. In contrast the chitosan salts of the invention are physiologically without any objection and cannot involve undesired reactions with the other components of the setting lotion.

A further advantage of the compounds of the invention is that they can be used in the form of purely aqueous solutions and nevertheless even in case of higher air humidity do not result in sticking of the hair as this is the case with the otherwise used conventional water-soluble resins. These water-soluble forms of the compounds of the invention can particularly be used with persons having a sensitive scalp in which case the usually used alcohol-containing setting lotions cannot be employed because of a burning sensation on the skin of the head.

The present invention also for the first time makes it possible to obtain a setting effect with thin, soft, dangling hair without having any undesirable effects such as an unnatural feel and a dull appearance of the hair.

The compounds of the invention are aqueous or aqueous-alcoholic solutions which are characterized by their contents of water-soluble salts of chitosan. As alcohols there can be used lower alcohols which are normally used for cosmetic purposes such as ethyl alcohol and isopropyl alcohol. The water-soluble chitosan salts should be present in the preparations in a concentration of 0.05 to 4.0% by weight, preferably between 0.5 and 1.5% by weight.

The chitosan is a high polymer amine and adapted to form salts with acids. It is made by alkaline deacetylation of chitin. The complete deacetylation is difficult since the alkali during the reaction penetrates the chitin particles only imperfectly. A virtually acetyl-free chitin, that is pure chitosan, can be obtained only by repeated alkali treatment or by fractionating. The chitosan commercially available therefore constitutes a more or less deacylated product with a chitosan contents of about 70 to 90% by weight. These commercial products as well as products with a higher contents of chitosan can be used for the purposes of the invention equally well.

By neutralization of the free amino groups of the chitosan with acids the corresponding salts can be obtained. According to the present invention, however, the salts can only be employed if they are soluble in water. Suitable acids for making the salts are for instance hydrochloric acid, formic acid, acetic acid, lactic acid, glycolic acid, malonic acid, thioglycolic acid, benzoic acid, adipic acid, citric acid, benzenedisulfonic acid and chlorosulfonic acid. Preferred for the purposes of the invention are the salts of formic acid, acetic acid and lactic acid.

The amount of acid preferably is chosen to obtain sufficient neutralization of the free amino groups of the initial chitosan. Thus for instance in order to form an aqueous solution of 1 gram of chitosan (having 90% of free amino groups) 3.36 grams of 10% acetic acid are necessary. A small excess of the acid during the neutralization has no effect on the usefulness of the final compound.

The invention also embraces hair setting preparations of the type described which at the same time include directly acting dyestuffs in order to obtain a setting and dyeing of the hair at the same time. These preparations are usually sold as color fixation agents or tinting agents. Among these color fixatives which may be used individually or as mixtures the following classes are mentioned here by way of illustration: aromatic nitro dyes (for instance 1,4-diamino-2-nitrobenzene), azo dyes (for instance C.I. Acid Brown 4), anthraquinone dyes (for instance C.I. Disperse Violet 4) and triphenylmethane dyes (for instance C.I. Basic Violet 1). The dyes of these groups according to their substituents may have acid, nonionic or basic character. Their total concentration in the preparation normally is between about 0.05 and 2.0% by weight.

The preparations of the invention may of course also include additional cosmetic additives such as perfuming oils, bactericides and fungicides, combing-improving substances etc.

The preparations may be applied also by means of a spray dispenser or other spray devices or in mixture with a conventional propelling gas from a pressure container.

During the application the setting lotions of the invention and the results obtained thereby can further be improved by giving the hair an alkaline aftertreatment. Such alkaline aftertreatment surprisingly does not reduce the desirable coating or filming properties discussed before but even increases adhesion of the coating to the hair so that even after washing of the hair with a customary shampooing the permanence of the style set after the washing operation is guaranteed and the use of a special hair setting agent which otherwise is customary following the shampooing is not necessary.

The alkaline treatment can be effected with an aqueous or aqueous-alcoholic solution containing such as for instance ammonia, organic amines like monoethanoamine, diethanolamine, triethanolamine or other alkaline reacting compounds, for instance basic reacting salts such as trisodium phosphate or sodium carbonate. The alkali contents should preferably be about between 0.3 and 2.0% by weight.

The carrier material for the alkaline instead of a solution may also be in form of an emulsion or a gel.

The following examples further illustrate the invention:

EXAMPLE 1

| | |
|---|---|
| 1.0 g | chitosan (having 90% free amino groups) |
| 3.36g | acetic acid (10%) |
| 0.1 g | sorbic acid |
| 95.54g | water, completely desalted |
| 100.00g | |

20 ml of this solution are spread on the washed, towel-dry hair and the hair is then set and dried as customary.

EXAMPLE 2

| | |
|---|---|
| 0.6 g | chitosan (having 90% free amino groups) |
| 1.56g | formic acid (10%) |
| 25.0 g | isopropanol |
| 72.84g | water, completely desalted |
| 100.00g | |

20 ml of this solution are spread on the washed, towel-dry hair and the hair is then set and dried as customary.

EXAMPLE 3

| | |
|---|---|
| 1.5 g | chitosan (having 90% free amino groups) |
| 7.4 g | lactic acid (10%) |
| 0.1 g | sorbic acid |
| 91.0 g | water, completely desalted |
| 100.0 g | |

20 ml of this solution were spread on the washed, towel-dried hair and the hair was set and dried as customary.

EXAMPLE 4

| | |
|---|---|
| 1.0 g | chitosan (having 90% free amino groups) |
| 3.36 g | acetic acid (10%) |
| 0.1 g | cetyltrimethylammoniumchloride (50% aqueous-alcoholic solution) |
| 0.05 g | C.I. Basic Violet 1 |
| 95.49 g | water, completely desalted |
| 100.00 g | |

20 ml of the solution was spread on the washed, towel-dried hair and the hair was then set and dried as customary. The hair thereafter exhibited a slight bluish tint.

ALKALIZING OF HAIR a) Alkalizing agent in the form of a solution

| | |
|---|---|
| 1.00 g | ammonia solution (25%) |
| 99.00 g | water, completely desalted |
| 100.00 g | |

After treating the hair according to one of the examples 1 to 4 the hair can then be alkalized by moistening the set hair thoroughly prior or after drying with about 20 to 30 ml of the alkalizing solution followed by drying without rinsing.

The following examples will show that alkalization with an alkalizing agent can also be carried out with the agent in a gel or emulsion form. In that case 20 g of the setting agent according to one of the examples 1 to 4 are well spread on the washed and towel-dry hair and the hair is dried under the drying hood. Thereafter, about 50 to 60 g of an alkalizing agent formed according to the following example b) to d) are well distributed on the dry hair and permitted to act on the hair for about 3 minutes whereupon the hair is rinsed with water and is set and dried as customary.

b) Alkalizing agent in the form of a gel

| | |
|---|---|
| 0.7 g | carboxylic vinyl polymer |
| 97.6 g | water, completely desalted |
| 1.7 g | ammonia solution (25%) |
| 100.0 g | | c) Alkalizing agent in the form of an emulsion

| | |
|---|---|
| 5.0 g | oleylcetylalcohol, oxyethylated with 7 to 8 mols of ethylene oxide |
| 15.0 g | paraffinum liquidum |
| 78.5 g | water, completely desalted |
| 1.5 g | monoethanolamine |
| 100.0 g | |

| d) | Alkalizing agent in the form of an emulsion |
|---|---|
| | 5.0 g cetylstearylalcohol |
| | 2.0 g cetyltrimethylammoniumchloride (50% aqueous-alcoholic solution) |
| | 91.5 g water, completely desalted |
| | 1.5 g trisodium phosphate |
| | 100.0 g |

All percentages used in this application are intended to refer to percentages by weight.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A process of setting the hair comprising applying to the hair a lotion wherein the active component is an aqueous or aqueous-alcoholic solution of a film-forming resin which resin contains 0.05 to 4% by weight of a water soluble salt of chitosan as the film-forming component, the said chitosan salt being obtained by reacting chitosan or a chitin product containing about 70–90% by weight of chitosan with a sufficient amount of an acid to neutralize the free amino groups present on chitosan and to form a water-soluble salt thereof.

2. The process of claim 1 wherein the chitosan salt is a salt of hydrochloric acid, formic acid, acetic acid, lactic acid, glycolic acid, malonic acid, thioglycolic acid, benzoic acid, adipic acid, citric acid, benzenedisulfonic acid or chlorosulfonic acid.

3. The process of claim 1 which contains the chitosan salt in an amount of 0.5 to 1.5% by weight.

4. The process of claim 1 wherein the hair setting lotion includes a hair dye in an amount of about 0.05 to 2.0% by weight of the total composition.

5. A process of setting the hair as defined in claim 1 wherein the lotion is applied to the washed and towel-dry hair followed by an alkalizing aftertreatment with an aqueous or aqueous-alcoholic solution, emulsion or gel of a compound selected from the group consisting of ammonia, an organic amine, and a basic reacting salt, the hair being set and dried before or after the alkalizing treatment.

6. The process of claim 5 wherein the alkalizing agent is applied to the hair in form of a solution in an amount of 20 to 30 ml.

* * * * *